United States Patent [19]

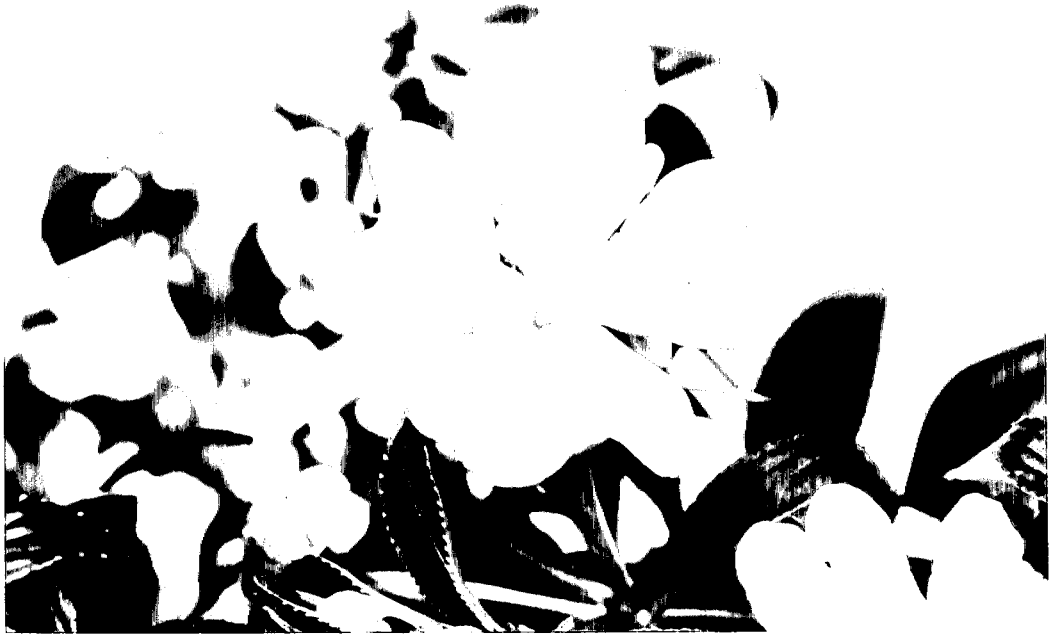

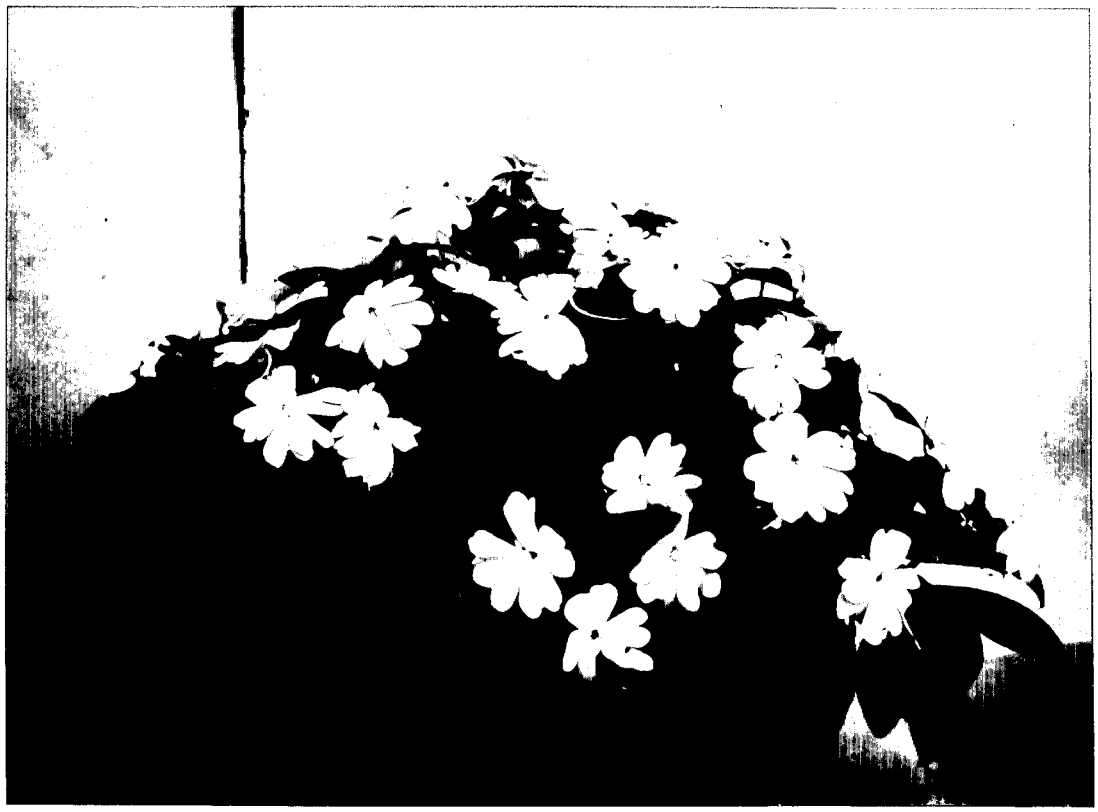

Hope

[11] Patent Number: Plant 5,698

[45] Date of Patent: Mar. 25, 1986

[54] IMPATIENS PLANT NAMED VISTA IMPATIENS NO. 44

[75] Inventor: Claude Hope, Cartago, Costa Rica

[73] Assignee: Pan American Plant Co., Parrish, Fla.

[21] Appl. No.: 566,504

[22] Filed: Dec. 29, 1983

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Schwartz, Jeffery, Schwaab, Mack, Blumenthal & Evans

[57] ABSTRACT

A new and distinct cultivar of impatiens plant known by the cultivar name Vista Impatiens No. 44, and characterized by its large and brilliant lavender colored flowers with a white eye; profuse blooming, dark green foliage, compact, dense and spreading form, good self-branching habit, and moderate rate of growth, making it ideal for hanging baskets, pot culture and bedding plant use.

2 Drawing Figures

The present invention relates to a new and distinctive cultivar of impatiens plant, botanically known as Impatiens, and known by the cultivar name Vista Impatiens No. 44.

The new cultivar was developed by me from a planned program of hybridization the purpose of which was to obtain a series of plants having a wide range of colors and very large flowers derived from the New Guinea complex of species collected by the Longwood Garden Expedition of 1970. The new cultivar was selected in 1981, and designated as seedling No. 1588-664-7-2. The new cultivar resulted from crossing seedling No. 1588-3 (from Impatiens Schlecterii P.I. 354260)×1664-5 (from Impatiens Variety Tangerine).

Asexual reproduction by terminal or stem cuttings taken by me at Cartago, Costa Rica has shown that the unique features of the new cultivar are stabilized and are reproduced true to type in successive propagations.

The following characteristics distinguish the new cultivar from both its parent varieties and other cultivated impatiens of this type known and used in the floriculture industry:

1. Vista Impatiens No. 44 was selected primarily for its brilliant lavender flowers, each of which has a white eye in the center of the flower.
2. Flower size is large (58–60 mm.).
3. Plant flowers profusely under optimum conditions (80° F. days — 60° F. nights).
4. Rate of growth is moderate, producing in 6–8 weeks in a 5½" pot a saleable plant 18–25 cm. tall and 20–25 cm. in diameter when grown under full sun in the fall, winter and spring and under light shade in the summer in Florida.
5. Plant is compact and dense (38–45 cm. tall when full grown) and spreading (45–60 cm. diameter), making it suitable for hanging baskets, pot culture and bedding plants.
6. Exhibits good self-branching habits.
7. Dark green foliage provides a striking contrast to lavender flowers.

In the accompanying drawings, Sheet 1 comprises a color photograph illustrating the overall appearance of the new cultivar, with the flower color in Sheet 1 being somewhat more pink than the actual flower color. Sheet 2 is an enlarged black and white photograph, with the true flower color being illustrated on one flower.

The following is a detailed description of my new impatiens cultivar based on plants produced under commercial practice in Cortez and Parrish, Fla. The plants were grown outdoors in full sun during the fall, winter and spring months and under light shade during the summer months. Color references are made to The Royal Horticultural Society Colour Chart except where general terms of ordinary dictionary significance are used.

Parentage: Seedling No. 1588-3 (from Impatiens Schlecterii P.I. 354260)×1664-5 (from Impatiens Variety Tangerine).

Propagation:

A. *Type cutting.*—Tip cuttings with 5 cm. stems.

B. *Time to initiate roots.*—10–14 days at 27° C. summer, 12–16 days at 18° C. winter.

C. *Rooting habit.*—Abundant and fibrous.

Plant description:

A. *Form.*—Compact and dense (38–45 cm. tall when full grown) and spreading (45–60 cm. diameter), producing a low dome-shaped plant.

B. *Habit of growth.*—Rate of growth moderate for this type of plant. Vegetative shoots are formed at the lower nodes and flowers at the higher nodes.

C. *Foliage description.*—Lower leaves opposite, higher leaves in whorls of 5–6. Leaves are simple. (1) Size: Average full grown leaf is 100 mm. long×40 mm. wide. Full grown leaves have petioles 40 mm. long. Young leaves have very short (5–7 mm. long) petioles. (2) Shape: Elliptic, apex acute to slightly acuminate, base attenuate. (3) Texture: Smooth surface, glabrous. (4) Margin: Serrulate. (5) Color: Young foliage, top side green 137C, under side close to yellow green 148C; mature foliage, top side green 137A, under side close to yellow green 148C. (6) Venation: Pinnate, main vein close to yellow green 145D.

Flowering description:

A. *Flowering habits.*—Very floriferous, flowers occurring progressively around the whorl of leaves. Flowers are large and single.

B. *Natural flowering season.*—Flowering is indeterminate and occurs throughout the year except for periods of high light and high temperature in Florida.

C. *Flower bud description.*—Conical, covered with 3 sepals. Upper sepals are 9 mm. long×7 mm. wide, apex acuminate; lower sepal is 12 mm. long×8 mm. wide, apex acuminate. Upper sepals are green, lower sepal colorless infused with green; green apex. Hollow spur (51 mm. long when full grown) is connected to base of lower sepal, and is green in color.

D. *Flowers borne.*—On peduncles 51 mm. long and green in color.

E. *Quantity of flowers.*—One flower per leaf occurring progressively around the whorl of leaves.

F. *Petals.*—

(1) *Shape.*—Top petal is heart-shaped with a broad rounded base. All other petals are heart-shaped with pointed bases. Occasionally a lobe is noted where the top of the petal curves to form the top of the heart-shape.

(2) *Color.*—Top side is violet 80C when opening, with a white eye in the center having a light pink stripe at the base of the two bottom petals. The main petal color fades to approximately 80D; under side, close to but somewhat lighter than 80D.

(3) *Number of petals.*—Five, with the middle and bottom petals being slightly united at the base on each side.

(4) *Size of flowers.*—Top petal is 21 mm. long×22 mm. wide; 2 middle petals 31 mm. long×20 mm. wide; 2 lower petals 32 mm. long×21 mm. wide. Total flower diameter is 58 mm.

G. *Reproductive organs.*—

(1) *Stamens.*—Five; with the lower stamen being shorter than the others. Stamens united in an asymmetrical tube surrounding and covering the ovary. (a) Anthers: Hooded, white in color. (b) Pollen color: Cream.

(2) *Pistils.*—(a) Stigma: Five pointed star, colorless. (b) Styles: Cream-green, very short. (c) Ovaries: 5, celled, size 5 mm. green in color.

Disease resistance: No general plant diseases noted. Insect problems can include the two-spotted spider mite which can cause foliar injury and thrips which can cause stunting and injury to the growing tip.

I claim:

1. A new and distinct cultivar of impatiens plant known by the cultivar name Vista Impatiens No. 44, as described and illustrated, and characterized by its large and brilliant lavender colored flowers with a white eye; profuse blooming, dark green foliage, compact, dense and spreading form, good self-branching habit, and moderate rate of growth, making it ideal for hanging baskets, pot culture and bedding plant use.

* * * * *